(12) United States Patent
Sasaki

(10) Patent No.: US 11,499,984 B2
(45) Date of Patent: Nov. 15, 2022

(54) PRETREATMENT APPARATUS AND ANALYSIS SYSTEM COMPRISING THE SAME

(71) Applicant: SHIMADZU CORPORATION, Kyoto (JP)

(72) Inventor: Akira Sasaki, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 488 days.

(21) Appl. No.: 16/601,729

(22) Filed: Oct. 15, 2019

(65) Prior Publication Data

US 2020/0116746 A1    Apr. 16, 2020

(30) Foreign Application Priority Data

Oct. 16, 2018 (JP) .............................. JP2018-195408

(51) Int. Cl.
*G01N 35/00* (2006.01)
*G06F 3/04817* (2022.01)
(Continued)

(52) U.S. Cl.
CPC ..... *G01N 35/00722* (2013.01); *G03G 15/502* (2013.01); *G06F 3/0482* (2013.01); *G06F 3/04817* (2013.01); *G06Q 10/0633* (2013.01); *G16H 10/40* (2018.01); *G01N 2035/0091* (2013.01)

(58) Field of Classification Search
CPC . G03G 15/502; G06F 3/04817; G06F 3/0482; G06F 3/0481; G01N 2035/0091; G01N 35/0092; G01N 1/28; G01N 2035/00891
See application file for complete search history.

(56) References Cited

U.S. PATENT DOCUMENTS 9,341,638 B2 * 5/2016 Sarwar ............. G01N 35/00584
2007/0038411 A1 * 2/2007 Taki ................. G01N 35/00722
702/182
(Continued)

FOREIGN PATENT DOCUMENTS

JP    WO2016/002032 A1    1/2016
JP    WO2016/006097 A1    1/2016
(Continued)

*Primary Examiner* — Cao H Nguyen
(74) *Attorney, Agent, or Firm* — Sughrue Mion, PLLC

(57) ABSTRACT

A display unit of the present invention displays icons respectively for a series of process steps of a pretreatment unit and an analysis device on a setting screen. The display unit displays a first shutdown icon for a first shutdown step and a second shutdown icon for a second shutdown step in association with the icons respectively for the series of process steps, the first shutdown step being performed when the pretreatment unit and the analysis device end process steps without causing an error, the second shutdown step being performed when the pretreatment unit and the analysis device end the process steps as an error is caused while the process steps are performed. When a user selects any one of these icons, the display unit displays an input screen on the setting screen for inputting the setting information for the process step corresponding to the selected icon.

10 Claims, 16 Drawing Sheets

(51) Int. Cl.
*G06F 3/0482* (2013.01)
*G06Q 10/06* (2012.01)
*G16H 10/40* (2018.01)
*G03G 15/00* (2006.01)

(56) References Cited

U.S. PATENT DOCUMENTS

| | | | |
|---|---|---|---|
| 2008/0046208 A1* | 2/2008 | Okuno | G16H 40/40 |
| | | | 422/68.1 |
| 2013/0009988 A1* | 1/2013 | Tokunaga | G01N 35/00871 |
| | | | 345/660 |
| 2014/0147335 A1 | 5/2014 | Sarwar et al. | |
| 2016/0266074 A1* | 9/2016 | Ueno | G01N 30/06 |
| 2017/0067922 A1* | 3/2017 | Antoni | G01N 35/00613 |
| 2017/0138824 A1 | 5/2017 | Hanafusa et al. | |
| 2017/0168027 A1 | 6/2017 | Hanafusa et al. | |
| 2017/0284981 A1 | 10/2017 | Hanafusa et al. | |
| 2018/0196016 A1 | 7/2018 | Hanafusa et al. | |
| 2018/0252682 A1 | 9/2018 | Hanafusa | |

FOREIGN PATENT DOCUMENTS

| | | |
|---|---|---|
| JP | WO2016/017042 A1 | 2/2016 |
| JP | WO2016/035142 A1 | 3/2016 |
| JP | WO2017/006476 A1 | 1/2017 |
| JP | 2018-004327 A | 1/2018 |
| JP | 6332448 B2 | 5/2018 |
| JP | 6332449 B2 | 5/2018 |
| JP | 6332456 B2 | 5/2018 |
| JP | 6337966 B2 | 6/2018 |
| JP | 2018-146333 A | 9/2018 |
| WO | 2012/165229 A1 | 12/2012 |

* cited by examiner

FIG.4

| ANALYSIS CONDITION | CALIBRATION CURVE |
|---|---|
| E1 | K1 |
| E2 | K2 |
| E3 | K3 |
| ⋮ | ⋮ |

FIG.5

| ANALYSIS CONDITION | CALIBRATION CURVE | CALIBRATION CURVE ID | CALIBRATION CURVE CREATION DATE & TIME | REFERENCE SAMPLE ID | ANALYSIS RESULT | ANALYSIS DATE & TIME |
|---|---|---|---|---|---|---|
| E1 | K1 | I1 | T1 | H1 | J1 | S1 |
| E2 | K2 | I2 | T2 | H2 | J2 | S2 |
| E3 | K3 | I3 | T3 | H3 | J3 | S3 |
| ... | ... | ... | ... | ... | ... | ... |

FIG.16

| TYPE OF ANALYSIS DEVICE | ORDER OF PROCESS STEPS |
|---|---|
| A1 | B1 |
| A2 | B2 |
| A3 | B3 |
| ⋮ | ⋮ |

PRETREATMENT APPARATUS AND ANALYSIS SYSTEM COMPRISING THE SAME

BACKGROUND OF THE INVENTION

Field of the Invention

The present invention relates to a pretreatment apparatus linked to an analysis device, and an analysis system comprising the same.

Description of the Background Art

In an analysis system, various process steps such as a pretreatment followed by a main analysis followed by a post-treatment are performed in analyzing a sample. For each of these process steps, it is necessary to perform various settings, such as how many times cleaning is done, how many times measurement is done, in how much amount a reagent, is added, and the like. However, a conventional setting screen for performing these settings only displays an input screen for inputting the name of a process step to be set and setting information, and it is difficult for the user to recognize which one of a plurality of process steps is set and it is difficult for the user to understand what process step is performed before and after the process step that is set.

Accordingly, WO2012/165229 discloses an automatic analyzer that displays a work flow to help any user of the automatic analyzer to understand the flow and to also ensure that the user performs the work regardless of the user's familiarity with the automatic analyzer. This automatic analyzer automatically analyzes a sample to obtain the concentration of an item to be inspected, and displays a work flow necessary for measurement by a plurality of work steps.

SUMMARY OF THE INVENTION

However, WO2012/165229 describes a setting screen which is configured to display a screen for a process step on a reduced workflow display screen and display a screen for inputting, the setting information for that process step. Therefore, the setting screen of WO2012/165229 does not display the entire workflow indicating a series of process steps, that is, it does not provide maximized displaying of the workflow, and setting information cannot be input while the entire process is confirmed.

Moreover, according to WO2012/165229, while maximized displaying of a workflow can display the entirety of a workflow indicating a series of process steps, when a shutdown step for one process step is included that shutdown step is not displayed. Furthermore, displaying a screen for inputting the setting information for the shutdown step requires displaying a setting, screen for a process step higher in level than the shutdown step. That is, the screen for inputting the setting information for the shutdown step is nested in the setting screen for the higher process step, and it is cumbersome for the user to perform an operation for setting for the shutdown step and the user cannot easily recognize that the shutdown step is settable.

The present invention has been made in view of the above circumstances, and in one aspect provides a pretreatment apparatus allowing setting, information to be input while an entire process is confirmed, and an analysis system comprising the pretreatment apparatus.

According to one aspect of the present disclosure, a pretreatment apparatus comprises: a pretreatment unit configured to subject to a pretreatment a sample to be analyzed by an analysis device; an analysis condition input unit configured to receive an analysis condition input; a communication unit configured to transmit to the analysis device the analysis condition received by the analysis condition input unit; a control unit configured to control the pretreatment unit, and control the analysis device based on the analysis condition transmitted to the analysis device; a setting unit configured to set setting information for the pretreatment unit and the analysis device; a setting information input unit configured to receive the setting information to be set in the setting unit; and a display unit configured to display a setting screen for inputting the setting information at the setting information input unit. The display unit is configured to display icons each corresponding to a process step of a series of process steps of the pretreatment unit and the analysis device on the setting screen in such a manner that an order of performing the series of process steps can be specified. The display unit is configured to display an icon for a first shutdown step and an icon for a second shutdown step in association with the icons each corresponding to a process step of the series of process steps, the first shutdown step being performed when the pretreatment unit and the analysis device end the process steps without causing an error, the second shutdown step being performed when the pretreatment unit and the analysis device end the process steps as an error is caused while the process steps are performed. When the user selects one of the icons each corresponding to a process step of the series of process steps, the icon for the first shutdown step, and the icon for the second shutdown step, the display unit is configured to display an input screen on the setting screen for inputting the setting information for a process step corresponding to the selected icon.

Visually displaying on the setting screen for which process step a setting is allows the user to more easily provide setting. Furthermore, avoiding displaying the setting screen in a nested manner allows the user to recognize that the first shutdown step and the second shutdown step can be set.

In one aspect, the display unit is configured to change an order of arranging icons corresponding to process steps, depending on the type of the analysis device linked to the pretreatment apparatus.

This allows appropriate settings to be done depending on the type of the analysis device linked, and process steps that need to be set can be confirmed in a list.

In one aspect, regardless of the order of performing the process steps in the pretreatment unit and the analysis device, the display unit is configured to display an input screen of the process step corresponding to the selected icon.

This allows settings to be done for each process step regardless of the order of performing the process steps and the user can thus provide settings as the user desires.

In one aspect, the display unit is configured to display on the setting screen a start button for starting performance in the pretreatment unit and the analysis device, and the start button is selectable after the setting information to be set in the pretreatment unit and the analysis device is input.

This can prevent the pretreatment unit and the analysis device from performing process steps while no setting is done in the pretreatment unit and the analysis device.

In one aspect, the display unit is configured to change as desired an order of arranging, icons displayed on the setting screen.

This allows the order of arranging icons to be changed to an order which facilitates the user to provide setting.

In one aspect, when setting information is input on an input screen for setting a first process step, the display unit is configured to input and display setting information on an input screen for setting a second process step relevant to the first process step.

This can alleviate an operation done by a user to input setting information.

In one aspect, the series of process steps includes preparation, an analyte analysis, and a post-treatment, and the display unit is configured to display an icon for the preparation, an icon for the analyte analysis, and an icon for the post-treatment on the setting screen in a manner that can specify that the preparation is performed followed by the analyte analysis followed by the post-treatment.

Thus the user can recognize that the preparation, the analyte analysis and the post-treatment are performed in this order, and an input screen for inputting setting information for each of these process steps can be displayed.

In one aspect, the pretreatment apparatus and the analysis device is configured to perform a dummy analysis in which at least the series of process steps is performed without introducing in the pretreatment apparatus the sample to be analyzed, and the display unit is configured to display an icon on the setting screen for the dummy analysis.

The dummy analysis that allows at least the series of process steps to be performed without introducing in the pretreatment apparatus the sample to be analyzed can thus be performed, and an input screen for inputting the setting information for the dummy analysis can be displayed.

In one aspect, the pretreatment apparatus and the analysis device is configured to perform a standby step for a period of time after one analysis step ends before the subsequent analysis step starts, and the display unit is configured to display an icon on the setting screen for the standby step.

Thus a standby step can be performed for a period of time after one analysis step ends before the subsequent analysis step is performed, and an input screen for inputting the setting information for the standby step can be displayed.

In one aspect of the present disclosure, an analysis system comprises the pretreatment apparatus described above and an analysis device linked to the pretreatment apparatus.

An analysis system which provides the above-mentioned effect can thus be provided.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 4 shows an example of a first table of the present embodiment.

FIG. 5 shows an example of a second table of the present embodiment.

FIG. 16 shows an example of a third table of the present embodiment.

DESCRIPTION OF THE PREFERRED EMBODIMENTS

The present invention will now be described in embodiments in detail with reference to the drawings. In the figures, identical or corresponding components are identically denoted and will not be described repeatedly.

[Configuration of Analysis System]

Figure 1:
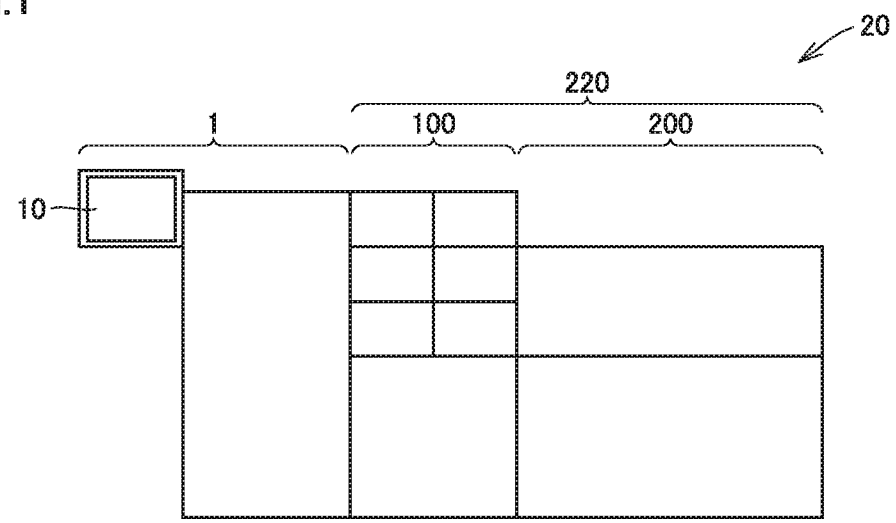
FIG. 1 is a schematic front view of an analysis system of the present embodiment.

FIG. 1 is a schematic front view showing a configuration example of an analysis system 20 according to the present embodiment. Analysis system 20 includes a pretreatment apparatus 1, an LC (liquid chromatograph) 100, and an MS (mass, spectrometer) 200. LC (liquid chromatograph) 100 and MS (mass spectrometer) 200 configure a liquid chromatograph mass spectrometer (LC/MS). LC 100 and MS 200 are also collectively referred to as an analysis device 220. Pretreatment apparatus 1 subjects a sample to a pretreatment and the thus pre-treated sample is sequentially introduced into analysis device 220 and analyzed. Furthermore, although not shown in FIG. 1, analysis system 20 also includes a computing device 90 (see FIG. 3).

Pretreatment, apparatus 1 subjects a sample to a predetermined pretreatment. The sample extracted through the pretreatment is introduced into LC 100 via an autosampler included in LC 100. Thus, pretreatment apparatus 1 has a transport mechanism for transporting to (or introducing into) analysis device 220 (or LC 100) the sample subjected to the pretreatment by pretreatment apparatus 1. Pretreatment apparatus 1 may not have a transport mechanism and the sample subjected to the pretreatment may be introduced into analysis device 220 manually by the user.

LC 100 is equipped with a column (not shown), and a sample component separated in a process of a sample passing through the column is sequentially introduced into MS 200. MS 200 includes an ionization unit that ionizes a sample introduced from LC 100, a mass spectrometer unit that analyzes the ionized sample, and the like. The mass spectrometer unit uses a calibration curve to analyze the concentration or the like of a sample to be analyzed, and outputs the concentration as an analysis result. Thus, analysis device 220 subjects to an analysis step a sample subjected to a pretreatment by pretreatment apparatus 1. The analysis step is also referred to as an "analyte analysis."

Pretreatment apparatus 1 includes a display unit 10 that displays a variety of types of information. Display unit 10 is typically a touch panel. A user (for example, an analyst) can perform an operation on a display screen of display unit 10 to perform an input for operations of pretreatment apparatus 1 and analysis device 220. The user can for example touch (or operate) each button or the like displayed on a display screen, as shown in FIGS. 7-14 etc., to cause a transition to a variety of types of screens or input a variety of types of setting information.

Figure 2:
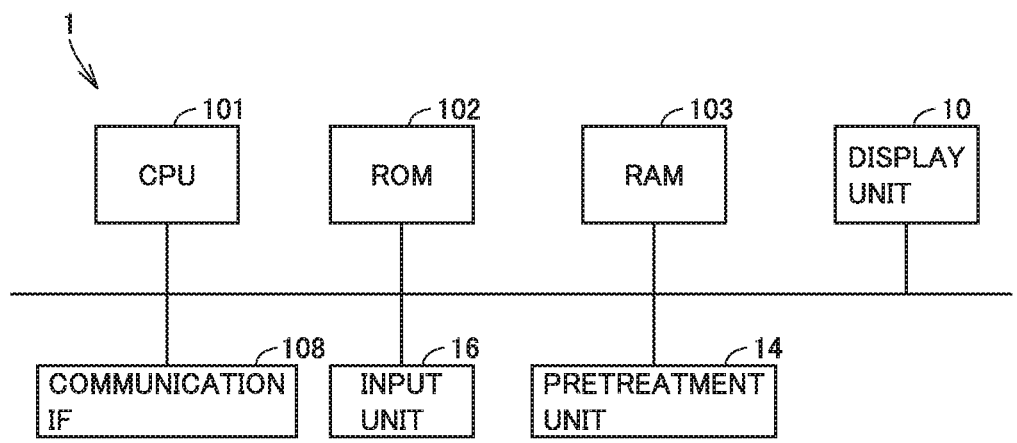
FIG. 2 is a hardware configuration example of a pretreatment apparatus of the present embodiment.

FIG. 2 shows a hardware configuration of pretreatment apparatus 1. Referring to FIG. 2, pretreatment apparatus 1 includes a central processing unit (CPU) 101 that executes a program, a read only memory (ROM) 102 that stores data in a non-volatile manner, a RAM (Random Access Memory) 103 that stores data in a volatile manner, and a communication IF 108 (also referred to as a communication unit) that communicates information with a device external to pretreatment apparatus 1. In the present embodiment, the external device is a computing device 90 shown in FIG. 3.

Pretreatment apparatus 1 includes display unit 10 that displays a variety of types of information, an input unit 16 that receives an input from a user, and a pretreatment unit 14 that performs a pretreatment. In the present embodiment, display unit 10 is a touch panel, and accordingly, display unit 10 and input unit 16 are integrated together. Note that, as a modification, when display unit 10 is not a touch panel and a configuration in which information is not input through a screen is applied, display unit 10 and input unit 16 are individually configured.

Figure 3:
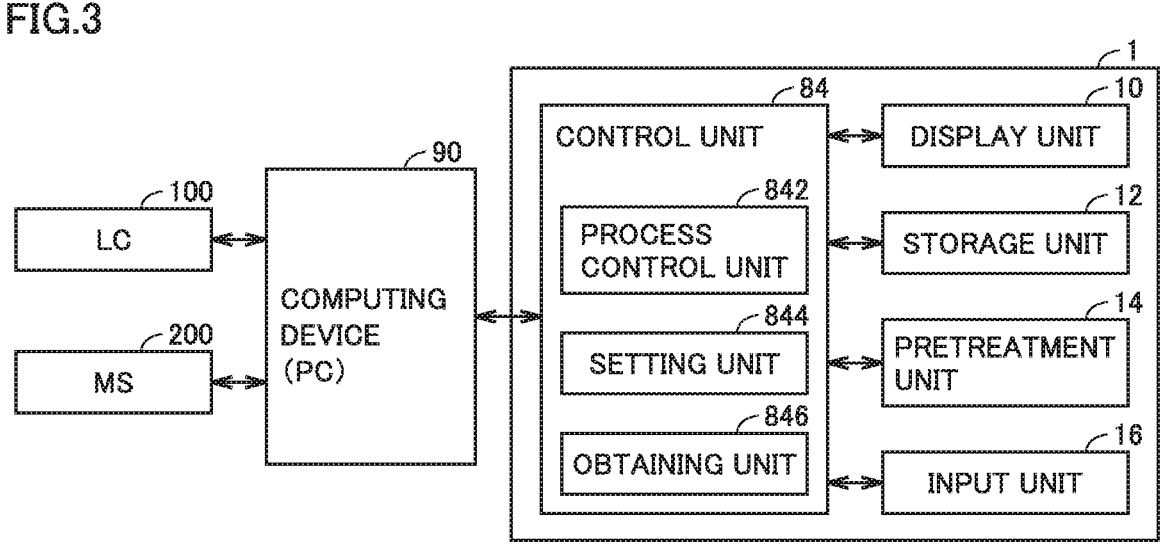
FIG. 3 is a functional configuration example of the analysis system of the present embodiment.

FIG. 3 is a diagram showing an example of a functional configuration of pretreatment apparatus 1. As shown in FIG. 3, pretreatment apparatus 1 includes a control unit 84, a display unit 10, a storage unit 12, a pretreatment unit 14, and an input unit 16. Control unit 84 executes a variety of types of control. As has been set forth above, display unit 10 displays a variety of types of information. Pretreatment unit 14 performs a pretreatment. In the pretreatment, typically, a sample of biological origin such as whole blood, serum, dried blood spot, and urine is subjected to a treatment such as sample dispensing, reagent dispensing, agitation, filtration and the like. Storage unit 12 stores a variety of types of information (such as a table described hereinafter). Input unit 16 receives an input from a user. Input unit 16 functions as an analysis condition input unit that receives an input of an analysis condition from the user. Further, input unit 16 functions as a setting information input unit for inputting setting information to be set in a setting unit 844.

Control unit 84 further has functions of a process control unit 842, setting unit 844, and an obtaining unit 846. Process control unit 842 controls pretreatment unit 14 and analysis device 220. Setting unit 844 sets setting information for pretreatment unit 14 and analysis device 220 controlled by process control unit 842. The setting information is, for example, information input by the user via input unit 16.

Pretreatment unit 14 performs a pretreatment based on the set setting information and the like. Analysis device 220 performs an analysis step based on the set setting information. Typically, an analysis condition is input by the user, as will be described hereinafter. The analysis condition includes an analysis condition for pretreatment apparatus 1 and an analysis condition for analysis device 220.

Further, pretreatment apparatus 1 can communicate a variety of types of information with LC 100 and MS 200 (or analysis device 220) via computing device 90. Computing device 90 is typically a PC (personal computer).

[Process by Analysis System]

A main process by analysis system 20 will now be described. FIG. 4 shows an example of a first table stored by pretreatment apparatus 1. In the example of the first table of FIG. 4, an analysis condition E and a calibration curve K are associated with each other. In the example of FIG. 4, for example, an analysis condition E1 and a calibration curve K1 are associated with each other. When the user or the like inputs that an analysis condition and a calibration curve are updated, the first table of FIG. 4 is updated according to the input. The first table is updated, for example, to increase a combination of an analysis condition and a calibration curve and decrease a combination of an analysis condition and a calibration curve. For creating a calibration curve, an analysis condition is input by the user and a reference sample is introduced into pretreatment apparatus 1 by the user. Thereafter, when the user inputs an operation to create the calibration curve, analysis system 20 creates the calibration curve based on the analysis condition and the reference sample.

FIG. 5 shows an example of a second table stored by pretreatment apparatus 1. In the second table of FIG. 5, a calibration curve K, a calibration curve creation date and time T, reference sample identification information H (also referred to as a reference sample ID), an analysis result J, and an analysis date and time S are associated with analysis condition E and calibration curve identification information I (also referred to as a calibration curve ID), and thus stored. In the example of FIG. 5, a calibration curve K1, a calibration curve creation date and time T1, reference sample identification information H1, an analysis result J1, and an analysis date and time S1 are associated with an analysis condition E1 and calibration curve identification information I1. The first table shown in FIG. 4 and the second table shown in FIG. 5 are both stored in storage unit 12.

Analysis condition E is information indicating the position of a probe or the like into which a sample or the like is injected, and a condition (or a setting) applied when pretreatment apparatus 1 and analysis device 220 analyze the sample. Calibration curve identification information I is information for identifying a calibration curve. A calibration curve creation date and time is a date and time when a calibration curve is created by analysis system 20. Reference sample identification information H is information about a sample used to create a calibration curve (i.e., a reference sample). Reference sample identification information H is typically information for identifying a reference sample. Analysis result J is derived by analysis system 20 and indicates a result of an analysis of a sample to be analyzed. In the present embodiment, the analysis result is, for example, the concentration of the sample to be analyzed. Analysis date and time S is a date and time when an analysis result is derived by analysis system 20.

Figure 6:
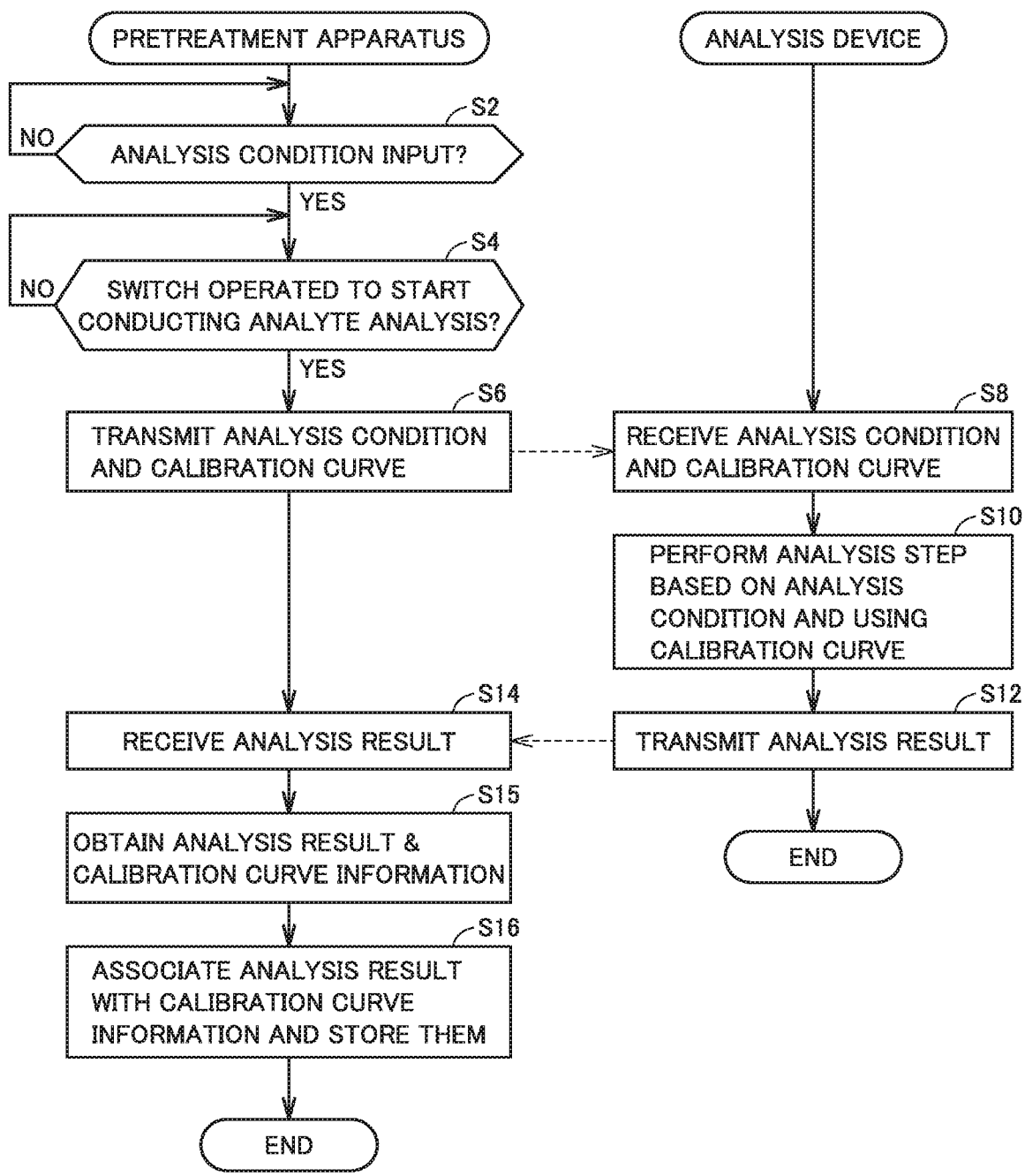
FIG. 6 is a flowchart of the analysis system of the present embodiment.

FIG. 6 is a flowchart of an example of a process done by pretreatment apparatus 1 and analysis device 220. An example of a process done by pretreatment apparatus 1 and analysis device 220 will be described with reference to FIG. 6. In step S2, control unit 84 of pretreatment apparatus 1 determines whether an analysis condition has been input by a user. In this scenario, the user inputs the analysis condition for example via a top screen shown in FIG. 7, as will be described hereinafter.

Subsequently, in step S4, control unit 84 determines whether a button 514 pressed to start conducting an analyte analysis, as shown in FIG. 5, as will be described hereinafter, has been pressed. Obtaining unit 846 refers to the first table of FIG. 4 and retrieves therefrom a calibration curve associated with the analysis condition input in step S2. In step S6, control unit 84 transmits to analysis device 220 the analysis condition input in step S2 and the calibration curve associated with the analysis condition.

In step S8, analysis device 220 receives the analysis condition and the calibration curve. In step S10, analysis device 220 subjects a sample to an analysis step, based on the analysis condition received in step S8, and using the calibration curve received in step S8.

In step S10, analysis device 220 initially calculates analysis data based on the analysis condition. The analysis data is typically a value in area (or a magnitude of a peak). Furthermore, analysis device 220 derives an analysis result based on the calibration curve (see FIG. 15 described hereinafter). The analysis result is typically a concentration.

The analysis data and the analysis result may be referred to as a first parameter and a second parameter, respectively.

In step S12, analysis device 220 transmits the analysis result obtained in step S10 to pretreatment apparatus 1. In step S14, control unit 84 receives the analysis result. In step S15, obtaining unit 846 obtains the analysis result received in step S14. In step S15, obtaining unit 846 further obtains the calibration curve transmitted in step S6 and calibration curve information about that calibration curve. Note that the calibration curve information includes a graph of the calibration curve per se (that is, calibration curve K), and information associated with the calibration curve. The information associated with the calibration curve includes, for example, calibration curve identification information I for identifying the calibration curve, calibration curve creation date and time T when the calibration curve was created, and reference sample identification information H used to create the calibration curve.

Subsequently, in step S16, control unit 84 associates the analysis result and calibration curve information obtained in step S15 and thus stores them. By performing step S16, control unit 84 incrementally updates the second table shown in FIG. 5.

[Display Screen]

Figure 7:
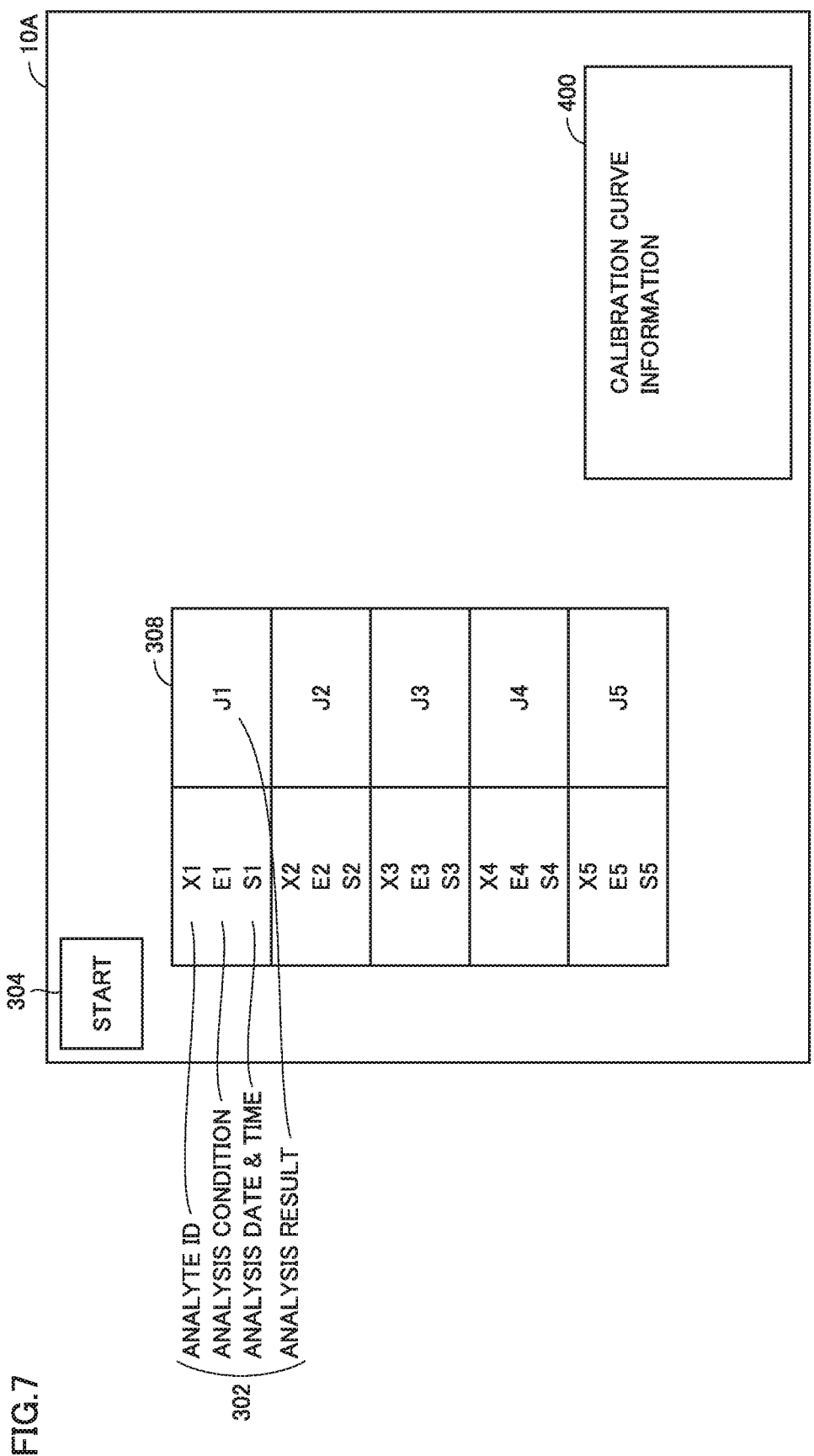
FIG. 7 is an example of a top screen of the present embodiment.

Hereinafter, an example of a display screen displayed in a display area 10A of display unit 10 will be described with reference to FIGS. 7 to 14. FIG. 7 shows an example of a top screen displayed by display unit 10. In the example of FIG. 7, an analysis result related information area 308 and a calibration curve information display area 400 are provided. In the example of FIG. 7, a start button 304, and analysis result related information area 308 displaying analyte identification information (also referred to as an analyte ID) or the like are displayed.

Display unit 10 displays one or more pieces of analysis result related information 302 in analysis result related information area 308. One piece of analysis result related information 302 includes analyte identification information X (or an analyte ID), analysis condition E, analysis date and time S, and analysis result J. In the example of FIG. 7, analyte identification information X, analysis condition E, and analysis date and time S are displayed in one cell of analysis result related information area 308.

Further, analysis result J is displayed in a cell adjacent to the one cell. In analysis result related information area 308, an analyte ID, and analysis condition E, analysis date and time S and analysis result J based on the second table of FIG. 5 are displayed. The analyte ID is an ID assigned for example when the analyte analysis start button is operated in step S4. That is, the analyte ID is an ID for uniquely identifying one sample analysis. The user may also input an analyzed sample's name rather than an analyte ID.

Calibration curve information display area 400 is provided at a lower right portion in the FIG. 7 top screen. Calibration curve information display area 400 will be described hereinafter with, reference to FIG. 14. The user can input the analysis condition described in step S2 of FIG. 6 by operating an analysis condition input button (not specifically shown) on the top screen of FIG. 7.

Figure 8:
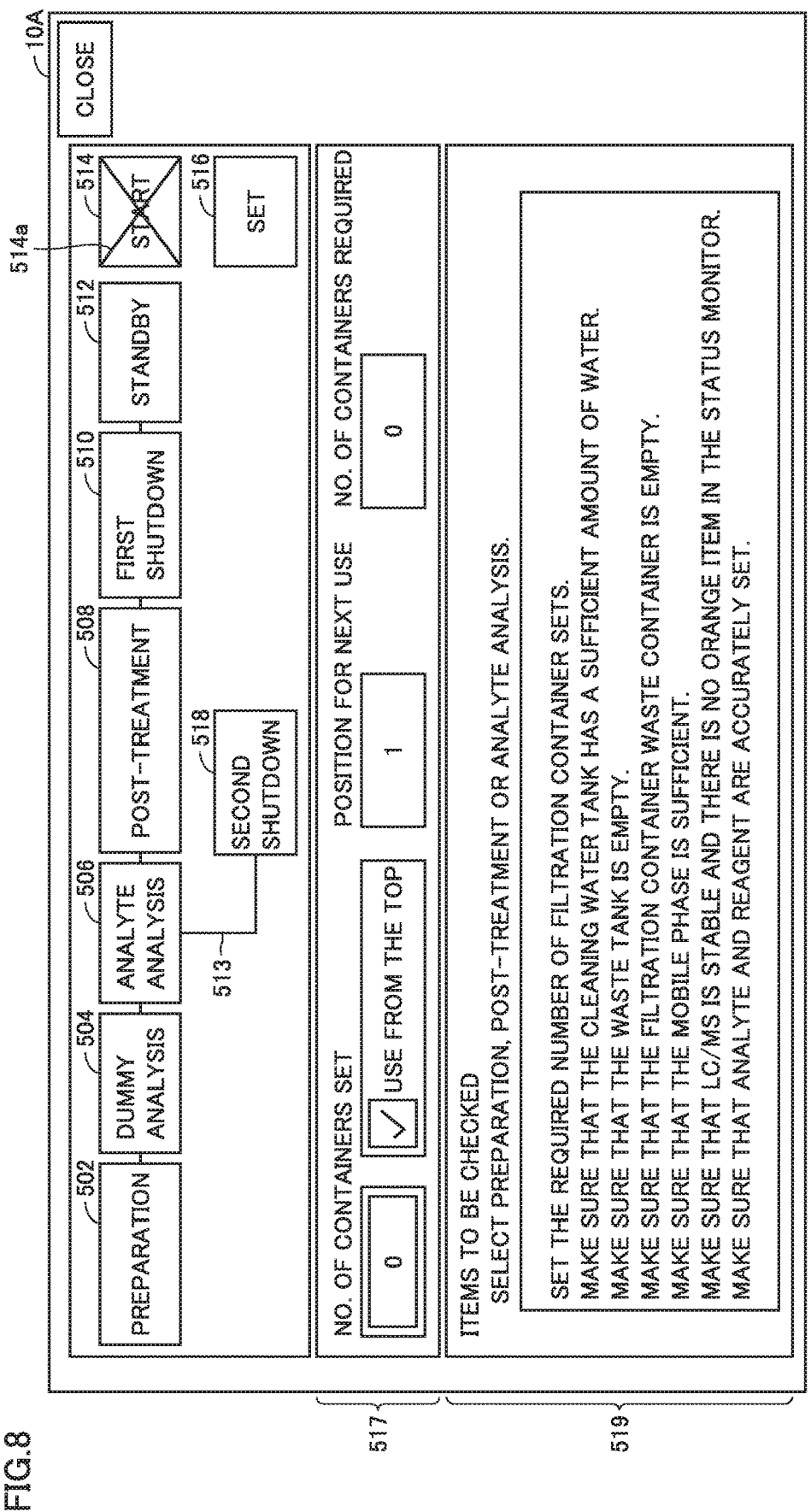
FIG. 8 is an example of a menu screen of the present embodiment.

The user presses start button 304 when starting an analysis step by pretreatment apparatus 1 and analysis device 220. When start button 304 is pressed, control unit 84 causes a transition to a menu screen. FIG. 8 is an example of the menu screen of the present embodiment.

The menu screen of FIG. 8 is a screen in which icons of a series of process steps done by analysis system 20 are displayed in an order of performing the process steps in pretreatment unit 14 and analysis device 220. In the example of FIG. 8, the process steps done in pretreatment unit 14 and analysis device 220 are preparation, a dummy analysis, an analyte analysis, a post-treatment, a first shutdown, standby, and a second shutdown. Pretreatment unit 14 and analysis device 220 perform the process steps initially by the preparation, followed by the dummy analysis, the analyte analysis, the post-treatment, the first shutdown, and the standby. In the example of FIG. 8, a preparation icon 502, a dummy analysis icon 504, an analyte analysis icon 506, a post-treatment icon 508, a first shutdown icon 510, a standby icon 512, and a second shutdown icon 518 are displayed. These icons are also collectively referred to as an icon group.

Furthermore, the preparation, the analyte analysis, and the post-treatment are also collectively referred to as a "series of the process steps". The series of the process steps, the dummy analysis, the first shutdown, and the second shutdown are also collectively referred to as "all of the process steps." That is, display unit 10 displays icons respectively of the series of the process steps (i.e., the preparation, the analyte analysis, and the post-treatment) (i.e., preparation icon 502, analyte analysis icon 506, and post-treatment icon 508), first shutdown icon 510, second shutdown icon 518, and standby icon 512.

Furthermore, display unit 10 displays the icons of the series of the process steps on a display screen (e.g., a menu screen, a setting screen 535 described hereinafter, etc.) in such a manner that an order in which the series of the process steps (all of the process steps) are performed can be specified. In the example of FIG. 8, from the left, display unit 10 displays preparation icon 502, dummy analysis icon 504, analyte analysis icon 506, post-treatment icon 508, first shutdown icon 510 and standby icon 512 in an order of performing the process steps in pretreatment unit 14 and analysis device 220. Further, immediately adjacent icons are connected by a line image.

Note that as a modification, the order in which all of the process steps are performed may be specified in a different manner. The different manner may for example be a manner in which preparation icon 502, dummy analysis icon 504, analyte analysis icon 506, post-treatment icon 508, first shutdown icon 510, and standby icon 512 are assigned numbers in order of performance and thus displayed.

Preparation icon 502 is an icon corresponding to the preparation. Dummy analysis icon 504 is an icon corresponding to the dummy analysis. Analyte analysis icon 506 is an icon corresponding to the analyte analysis. Post-treatment icon 508 is an icon corresponding to the post-treatment. First shutdown icon 510 is an icon corresponding to the first shutdown. Standby icon 512 is an icon corresponding to a standby step. The second shutdown icon 518 is an icon corresponding to the second shutdown.

When one of the icons is selected by the user (or when it is touched by the user), display unit 10 displays the selected icon in a manner different from that in which the other, non-selected icons are displayed (such that the selected icon is highlighted). Typically, display unit 10 displays the selected icon so as to be different from the manner in which the non-selected icons are displayed (e.g., different in color). This allows the user to recognize the icon that the user has selected.

The preparation and the post-treatment are process steps performed by the pretreatment apparatus 1. Further, the analyte analysis is a process step performed by pretreatment apparatus 1 and analysis device 220.

Analysis system 20 performs as the analyte analysis the step of analyzing a sample by pretreatment apparatus 1 and analysis device 220 (i.e., an analysis step). Analysis system 20 can perform the preparation and the dummy analysis prior to the analyte analysis.

The preparation includes, for example, the step of cleaning a probe (not specifically shown) into which a sample present in pretreatment apparatus 1 is injected. The pretreatment can remove impurity introduced into the probe, for example.

Hereinafter, the dummy analysis will be described. For example, when a mobile phase is switched, the column is switched, and/or a gradient initial concentration is changed, the column is filled with a mobile phase used before the switching is done, and an analysis may not be performed correctly. Accordingly, by performing the dummy analysis, an analysis without injection (for example, without any sample) can be performed, and the column can be equilibrated before analyzing a sample. In other words, the dummy analysis is a step which causes analysis system 20 to perform, without introducing any sample into analysis system 20, the same process as when a sample is introduced. In other words, when the dummy analysis is performed, all (or the series) of the process steps will be performed without introducing into pretreatment apparatus 1 any sample to be analyzed.

The analyte analysis is the step of analyzing a sample by pretreatment apparatus 1 and analysis device 220, as has been described above. The post-treatment includes, for example, the step of cleaning, when the analyte analysis ends, a probe (not specifically shown) into which a sample present in pretreatment apparatus 1 is injected. The post-treatment can prevent the sample or the like from remaining in the probe.

The first shutdown step is a step performed after the analyte analysis by analysis system 20 ends without causing any error and the post-treatment also ends. The first shutdown step stops (or shuts down) the process done by pretreatment apparatus 1. Note that the first shutdown step may shut down both pretreatment apparatus 1 and analysis device 220.

The standby step is a step of causing analysis system 20 to stand by after one analyte analysis ends before the next analyte analysis is performed. For example, the standby step is a step for smoothly starting a next analyte analysis after one analyte analysis ends.

The second shutdown step is the step of stopping the process steps of pretreatment apparatus 1 and analysis device 220 when an error occurs while pretreatment apparatus 1 and analysis device 220 perform the analyte analysis. This can prevent the analysis step from being continued while an error is caused. Analyte analysis icon 506 and the second shutdown icon are connected by a line image 513. This allows the user to intuitively recognize that the second shutdown is a shutdown executed during an analyte analysis (that is, a shutdown is done when an error occurs during the analyte analysis).

On the screen of FIG. 8, an input image 517 is displayed to allow usage information of pretreatment apparatus 1 to be input. Via input image 517, the number of containers installed or the like can be set in pretreatment apparatus 1.

On the screen of FIG. 8, a caution image 519 (of check items) is displayed to caution the user in using pretreatment apparatus 1 and analysis device 220. Caution image 519 is, for example, an image to caution the user in using analysis system 20. Caution image 519 of FIG. 8 displays a message "Select preparation, post-treatment, or analyte analysis." This can urge the user to select the preparation, the post-treatment, or the analyte analysis. In addition, caution image 519 also indicates such a message as "Set as many filtration container sets as necessary."

Display unit 10 displays on the setting screen of FIG. 8 performance start button 514 for performing process steps in the pretreatment unit and analysis device 220. When an icon is selected by the user and performance start button 514 is selected, a process step corresponding to the selected icon is performed.

However, performance start button 514 is adapted to be unselectable when none of the icons corresponding to the series of the process steps (i.e., the preparation, the post-treatment, and the analyte analysis), that is, preparation icon 502, post-treatment icon 508, and analyte analysis icon 506, is selected. "Performance start button 514 is unselectable" means that "pretreatment apparatus 1 does not accept an operation done to performance start button 514 by a user."

In the example of FIG. 8, an x image 514a is displayed on performance start button 514, and x image 514a is an image (or object) for making the user recognize that performance start button 514 is unselectable. Note that, as a modification, display unit 10 may display performance start button 514 in a different manner to indicate that the button is unselectable. For example, performance start button 514 may for example be displayed lighter than the other icons.

When an icon corresponding to a process step desired by the user is selected and performance start button 514 is operated by the user, analysis system 20 can be caused to perform the process step corresponding to the selected icon.

Figure 9:
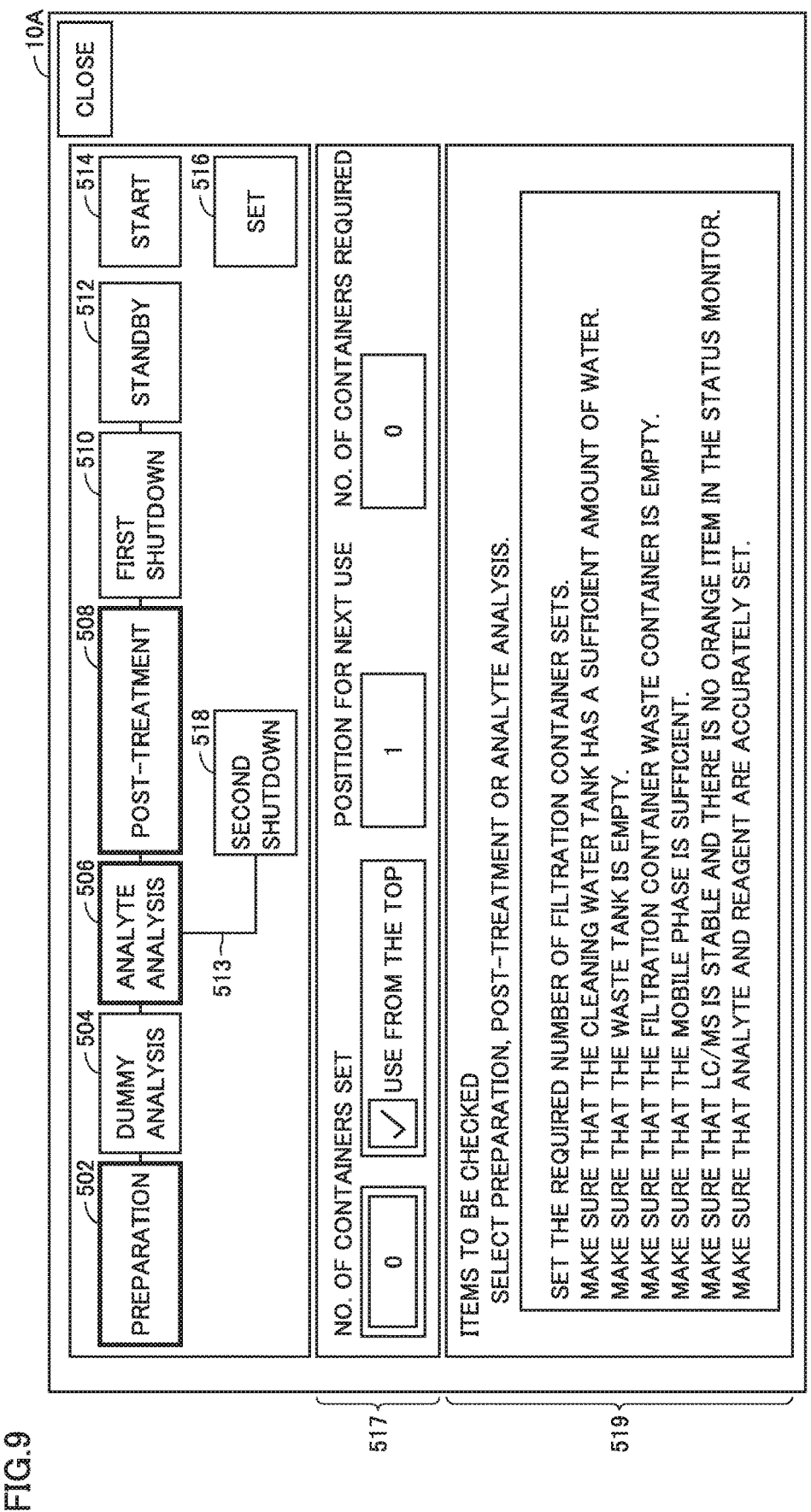
FIG. 9 is an example of a menu screen of the present embodiment.

FIG. 9 shows a state in which an icon is selected. In the example of FIG. 9, an icon selected by the user has its perimeter indicated by a thick line. The example of FIG. 9 shows the preparation, the analyte analysis, and the post-treatment selected. Analysis system 20 of the present embodiment allows the user to select one or more process steps to be started to be performed. In other words, analysis system 20 of the present embodiment allows the user to select one or more icons corresponding to process steps to be started to be performed. Display unit 10 displays a selected icon in a manner different than the other icons. In the example of FIG. 9 or the like, display unit 10 displays the perimeter of the selected icon by a thicker line than the other icons. Note that, as a modification, display unit 10 may display the selected icon in a color different than the other icons.

In this manner, analysis system 20 can perform one or more process steps selected by the user.

Figure 10:
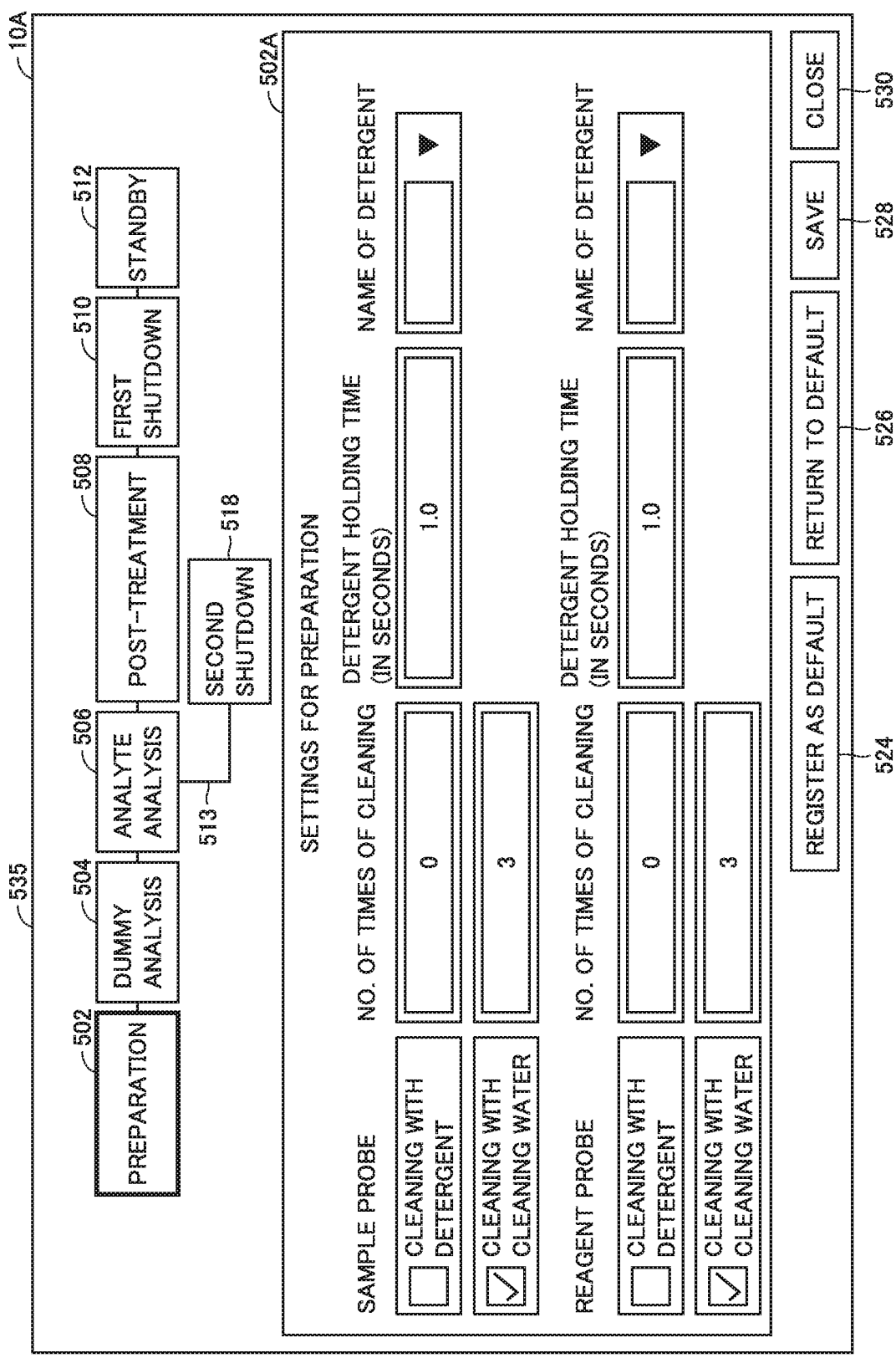
FIG. 10 is an example of a setting screen of the present embodiment.

Hereinafter, a setting button 516 shown in FIG. 8 will be described. When the user operates setting button 516, control unit 84 displays a setting screen. FIG. 10 shows an example of a setting screen 535. On the setting screen 535 of FIG. 10, the same icon group as that of FIG. 9 (that is, preparation icon 502, dummy analysis icon 504, analyte analysis icon 506, post-treatment icon 508, first shutdown icon 510, standby icon 512 and second shutdown icon 518) is displayed in the same manner as that in FIG. 9.

Furthermore, on setting screen 535, display unit 10 displays a selected icon in a manner different than the other icons and also displays an input screen corresponding to that selected icon.

Furthermore, in the present embodiment, setting screen 535 also displays an input screen for a predetermined process step. In the example of FIG. 10, the predetermined process step is the preparation. That is, in the example of FIG. 10, setting screen 535 also displays an input screen 502A for the preparation.

Input screen 502A for the preparation is a screen allowing the user to input setting information for the preparation. The setting information for the preparation is for example setting information for setting a method for cleaning a member (for example, a probe (not shown)) that pretreatment apparatus 1 has. An example of input screen 502A includes a screen allowing setting information, such as how many times the probe is cleaned, what type of detergent is used to clean the probe, etc., to be input as the method for cleaning the probe. Furthermore, on the input screen of the present embodiment, a black triangular mark is displayed, and when the triangular mark is selected, a list of items for which the triangular mark is displayed is displayed. The user can select a desired item from the list.

In addition to the input screen, a register as default button 524, a return to default button 526, a save button 528, and a close button 530 are displayed.

Register as default button 524 is a button for registering the setting information that is currently input on the input screen as a default. When the user operates register as default button 524, control unit 84 causes storage unit 12 to store the setting information that is currently input on the input screen as default information.

Return to default button 526 is a button for resetting the setting information currently input on the input screen to a default value. When the user operates return to default button 526, control unit 84 obtains a default value from storage unit 12 and reflects the default value on the input screen.

Save button 528 is a button for saving the setting information currently input on the input screen. When the user operates save button 528, setting unit 844 sets the setting information presented when save button 528 is operated. Thus, analysis system 20 performs the series (or all) of the process steps or the like based on the setting information thus set. The stored setting information is erased whenever an analyte analysis has once been performed.

Close button 530 is a button for closing the setting screen. When the user operates close button 530, the current screen returns to the menu screen (see FIG. 8).

When setting screen 535 is displayed and the user selects an icon corresponding to another process step, an input screen for the process step corresponding to the selected icon is displayed.

Figure 11:
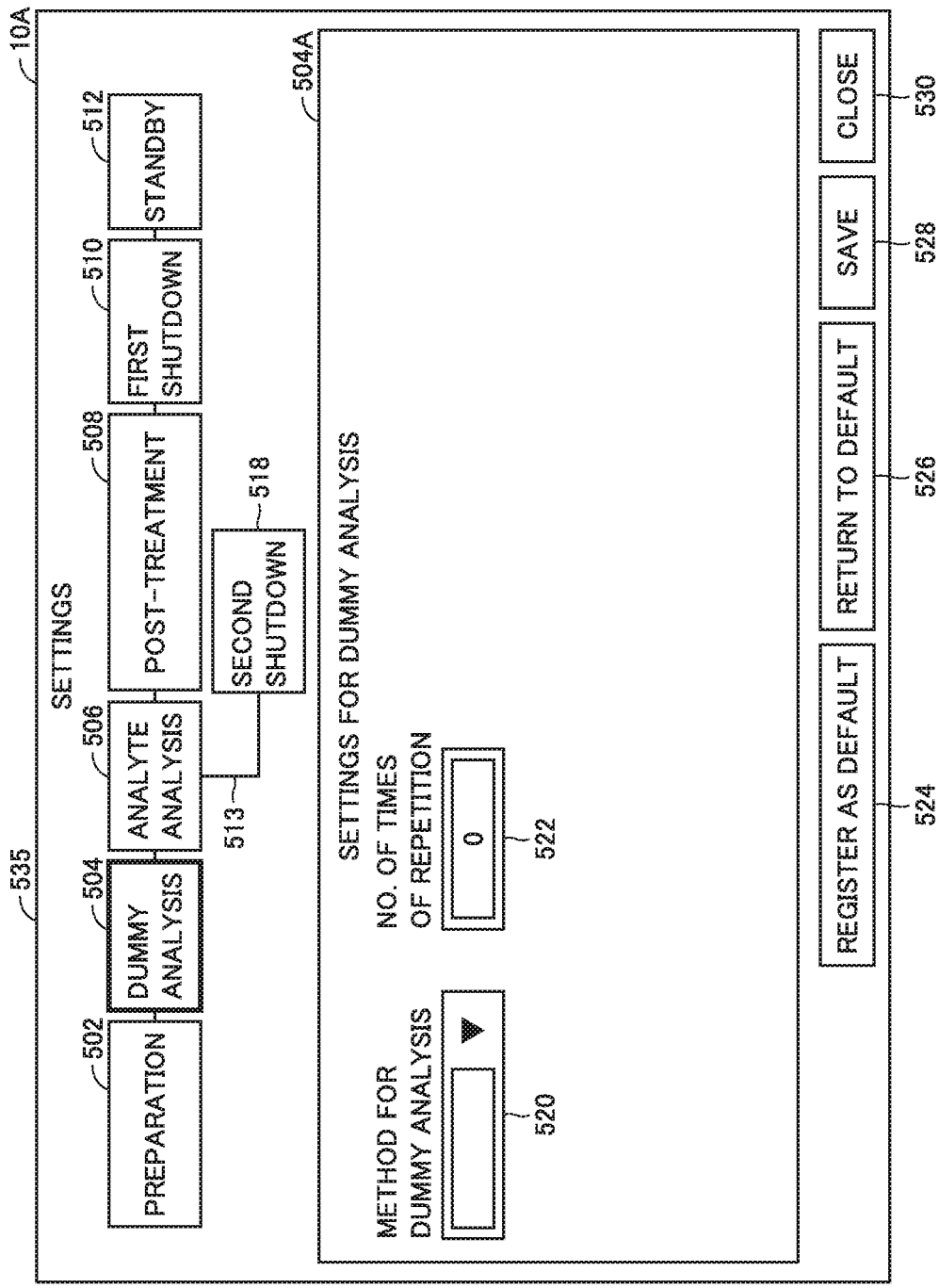
FIG. 11 is an example of a setting screen of the present embodiment.

FIG. 11 shows an example of displaying a dummy analysis input screen 504A when dummy analysis icon 504 corresponding to the dummy analysis is selected by the user. In the example of FIG. 11, dummy analysis input screen 504A is displayed. Dummy analysis input screen 504A displays an image 520 to which a method for the dummy analysis is input, and an image 522 to which how many times the dummy analysis is repeated (or performed) is input.

The method for the dummy analysis is to set a process step done during the dummy analysis by a member that pretreatment apparatus 1 and analysis device 220 have. For example, the method for the dummy analysis is to adjust the flow rate of a pump for the LC mobile phase of LC 100, the temperature of LC 100, and the like.

Figure 12:
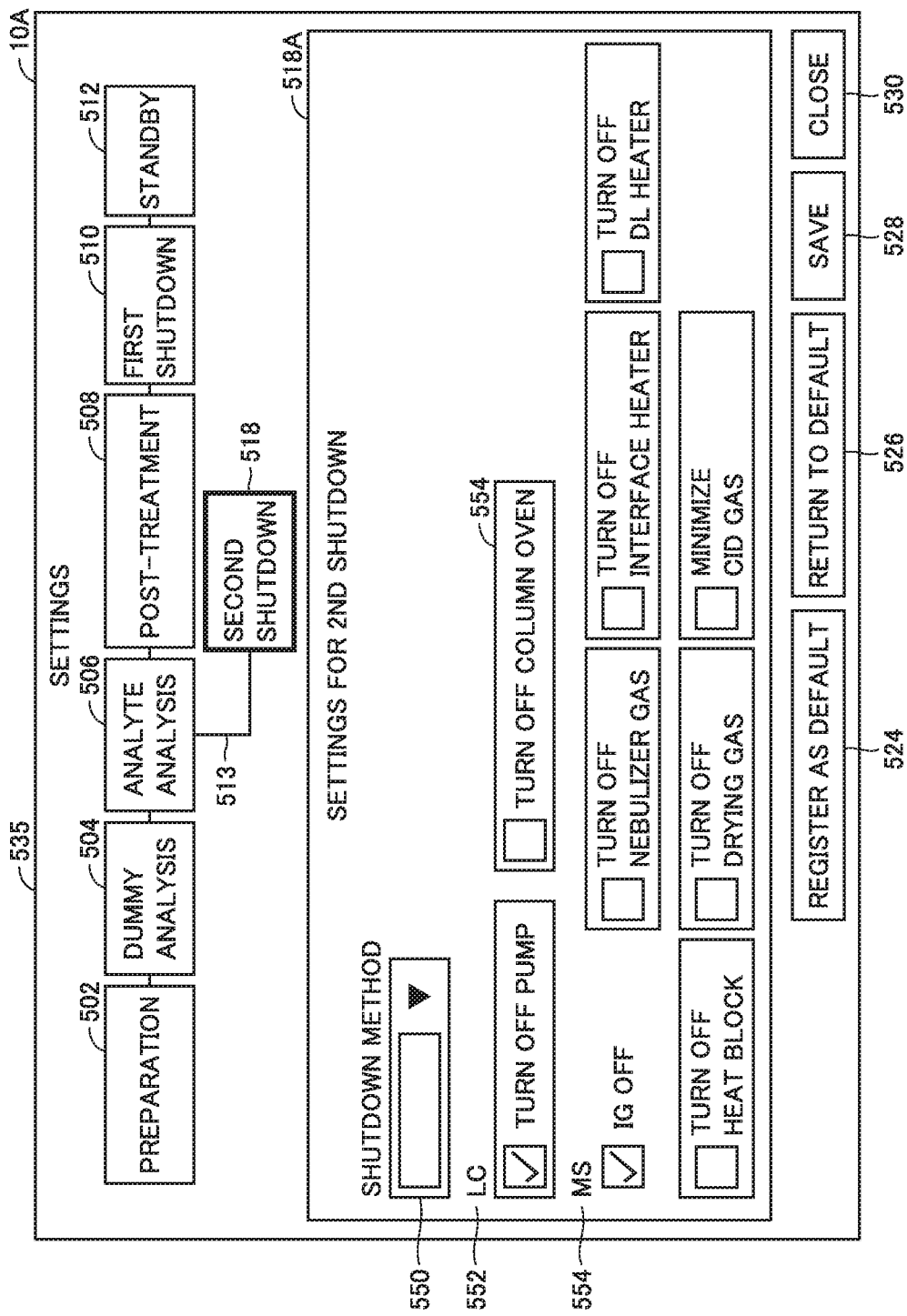
FIG. 12 is an example of a setting screen of the present embodiment.

FIG. 12 shows an example of displaying a second shutdown input screen 518A when second shutdown icon 518 is selected by the user. In the example of FIG. 12, on second shutdown input screen 518A, a second shutdown method image 550, an image 552 for the LC, and an image 554 for the MS are displayed.

Second shutdown method image 550 is an image in which a second shutdown method is input by the user. The second shutdown method is a method of shutdown executed when an error occurs while analysis system 20 performs an analysis.

The second shutdown method is, for example, to determine a period of time from when an error occurs to when a process step set in image 552 for the LC and that set in image 554 for the MS are performed.

Image 552 for the LC is an image for inputting control applied to each component of LC 100 when executing the second shutdown. In the example of FIG. 12, image 552 for the LC includes, for example, an image for inputting whether to turn off the pump of LC 100 and an image for inputting whether to turn, off a column oven.

Image 554 for the MS is an image for inputting control applied to each component of MS 200 when executing the second shutdown. In the example of FIG. 12, image 554 for the MS includes, for example, an image for inputting whether to turn off a nebulizer gas for MS 200 or the like.

In the present embodiment, image 552 for the LC and image 554 for the MS have a specification according to which setting information is input using a check box.

Figure 13:
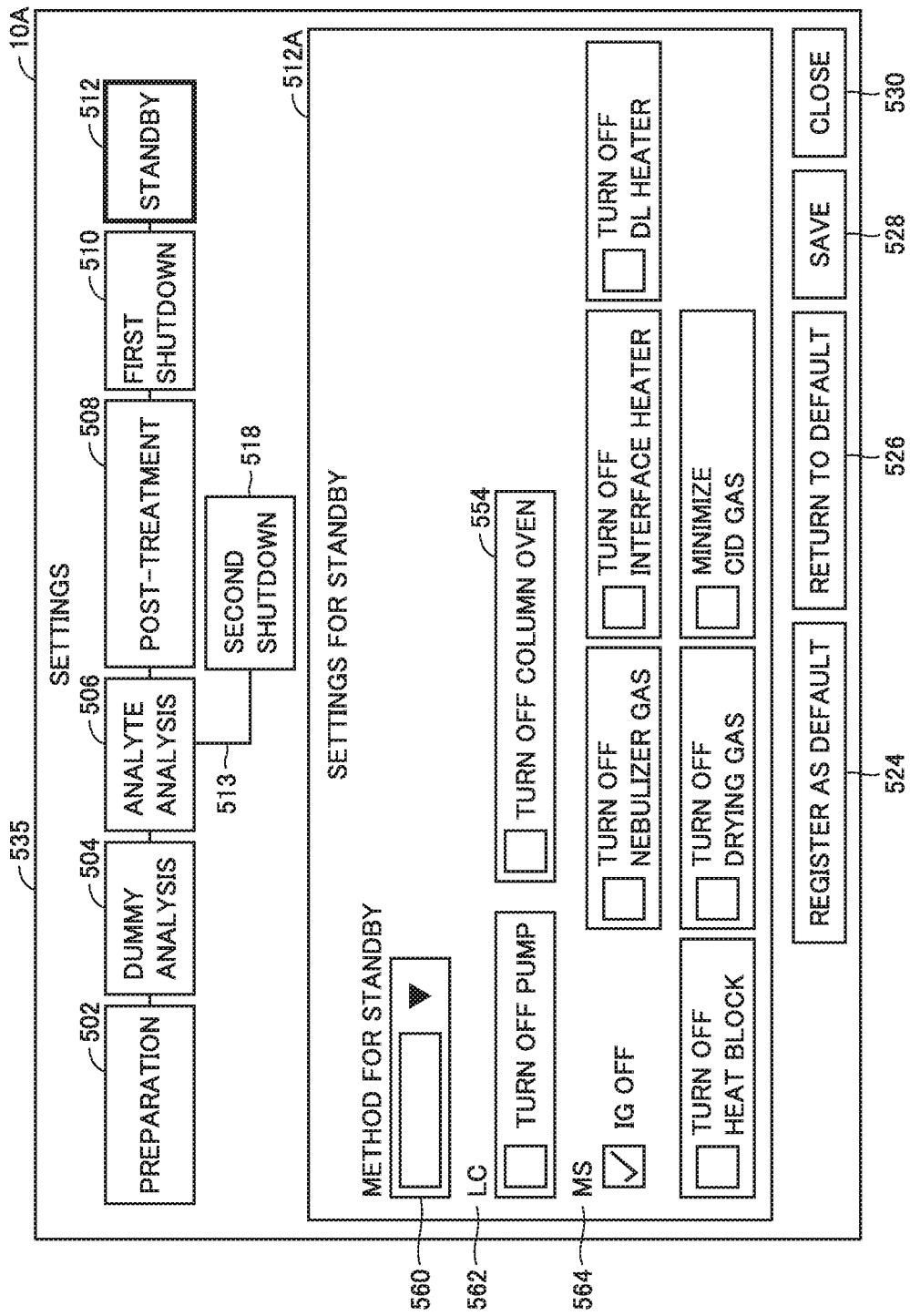
FIG. 13 is an example of a setting screen of the present embodiment.

FIG. 13 shows an example of displaying a standby input screen 512A when standby icon 512 is selected by the user. In the example of FIG. 13, on standby input screen 512A, a standby method image 560, an image 562 for the LC, and an image 564 for the MS are displayed.

Standby method image 560 is an image allowing the user to input a standby method. The standby method is a method for stopping analysis system 20 while waiting after one analyte analysis ends before the next analyte analysis is performed. In other words, the standby method specifies a method for causing analysis system 20 (or analysis device 220) to smoothly start the next analyte analysis when one analyte analysis ends. Furthermore, in other words, the standby method is a method that specifies whether a component of at least one of pretreatment apparatus 1 and analysis device 220 is put to sleep when one analyte analysis ends. Typically, the standby method includes a method which specifies whether to perform "a step to cause the pump that LC 100 has to pump out a substance in a small amount so that when starting the next analyte analysis, driving the pump is smoothly started." The standby method according to the present embodiment is identical to the second shutdown method. As a modification, the standby method according to the present embodiment may be different from the second shutdown method. Image 562 for the LC and image 564 for the MS are the same as image 552 for the LC and image 554 for the MS, respectively, described with reference to FIG. 12.

Note that an input screen for the setting information for the analyte analysis is not specifically shown. The input screen for the analyte analysis includes, for example, an image for inputting whether to set a bar code input by reading and inputting a bar code of a sample.

An input screen for the setting information about the post-treatment is for example identical to the input screen for the pretreatment shown in FIG. 10. Furthermore, an input screen for the first shutdown step is for example identical to the input screen for the second shutdown step shown in FIG. 12. The shutdown method of the first shutdown step includes, for example, a method that specifies whether a component of analysis device 220 is cleaned. The shutdown method for the first shutdown and the shutdown method for the second shutdown may be identical.

The screens in FIGS. 8 and 9 are also referred to as a "pre-setting screen" as they are screens immediately preceding setting screen 535.

Reference is again made to FIG. 7. On the top screen of FIG. 7, the user can select one piece of analysis result related information 302 out of a plurality of pieces of analysis result related information 302 shown in FIG. 7. For example, when the user touches an area of one piece of analysis result related information 302 of the plurality of pieces of analysis result related information 302, that one piece of analysis result related information 302 is selected. When the one piece of analysis result related information 302 is selected, display unit 10 displays the calibration curve information associated with the one piece of analysis result related information 302.

Figure 14:
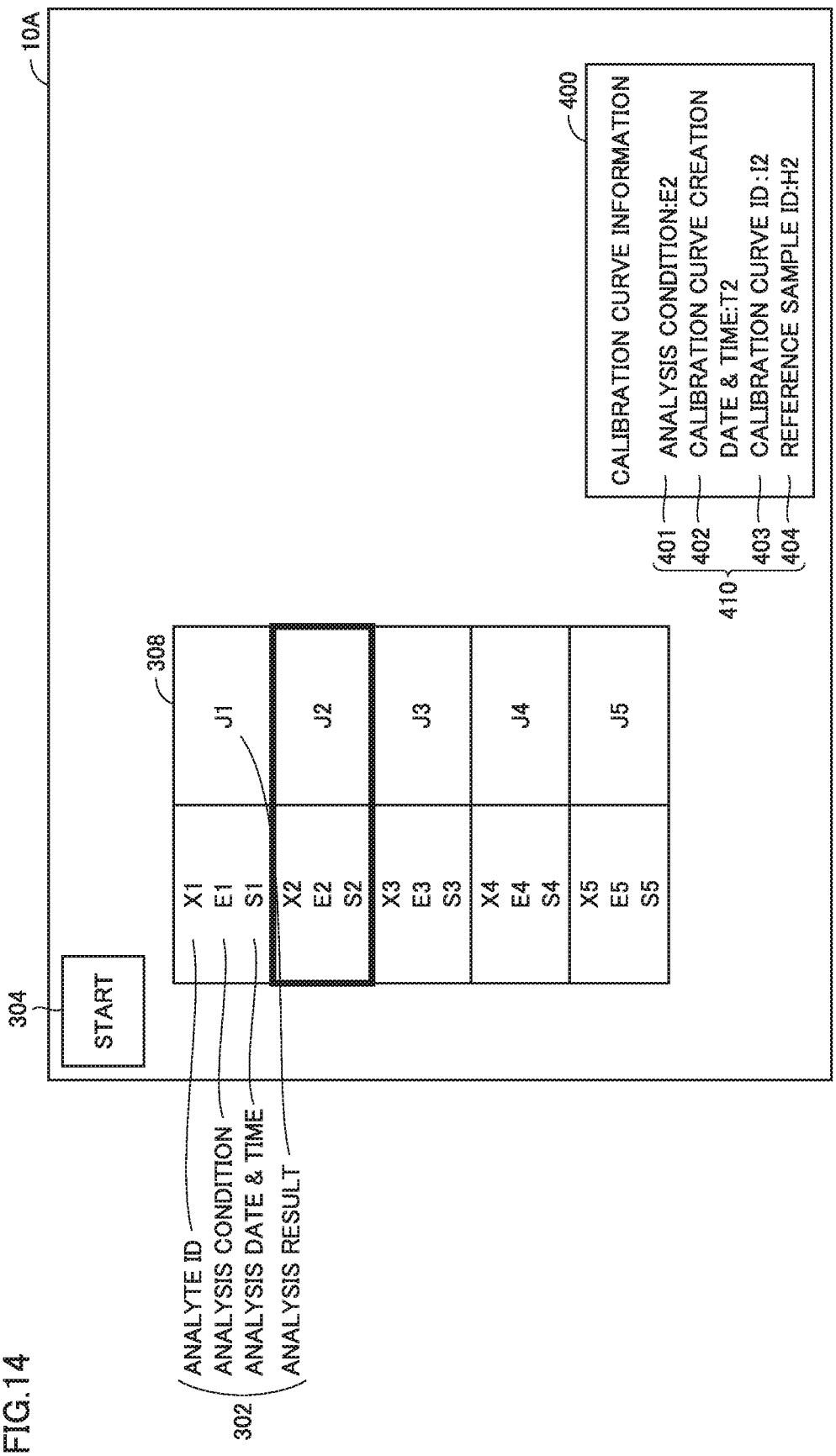
FIG. 14 is an example of a top screen of the present embodiment.

FIG. 14 shows an example of a top screen when calibration curve information is displayed. In FIG. 14, the cell of analysis result related information 302 selected has its perimeter indicated by a thick line. In the example of FIG. 14, analysis result related information 302 with an analyte ID of X2 is selected.

Calibration curve information 410 associated with analysis result related information 302 is displayed in calibration curve information display area 400. When input unit 16 receives a selection of one piece of analysis result related information 302, control unit 84 extracts analysis condition E of that one piece of analysis result related information 302 (in the example of FIG. 14, analysis condition E2). Control unit 84 refers to the second table (see FIG. 5) and therefrom extracts the calibration curve information associated with analysis condition E2 extracted, that is, calibration curve creation date and time T2, calibration curve identification information I2, and reference sample identification information H2. Display unit 10 displays analysis information E2 and together therewith the extracted calibration curve creation date and time T2, calibration curve identification information I2 and reference sample identification information H2 in calibration curve information display area 400 as calibration curve information 410.

Furthermore, the user can select, calibration curve information display area 400. When calibration curve information display area 400 is selected, control unit 84 displays the calibration curve (a calibration curve graph) of the calibration curve ID displayed in calibration curve information display area 400.

Figure 15:
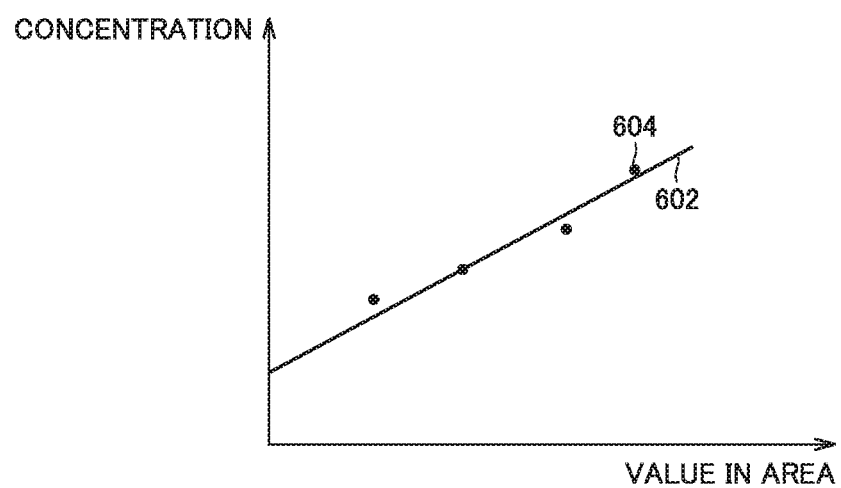
FIG. 15 shows an example of a graph of a calibration curve of the present embodiment.

FIG. 15 represents an example of a calibration curve (or a calibration curve graph). FIG. 15 is a graph 602 representing the calibration curve of calibration curve identification information I2. In the example of FIG. 15, the horizontal axis represents a value in area and the vertical axis represents concentration. In the example of FIG. 15, graph 602 representing a calibration curve and an analysis result 604 used when the calibration curve is created are associated with each other and displayed on the same screen. Based on a plurality of analysis results 604, graph 602 representing a calibration curve is created. Thus, the user can easily recognize a deviation between the graph of the calibration curve and analysis result 604 used when the graph of the calibration curve is created.

Effect of the Present Embodiment

Hereinafter, a configuration and effect of pretreatment apparatus 1 and analysis system 20 of the present embodiment will be described.

(1-1) As shown in FIGS. 10 to 13, display unit 10 displays setting screen 535 in which process steps are iconified in an order in which pretreatment apparatus 1 and analysis device 220 perform them. On setting screen 535, preparation icon 502, analyte analysis icon 506, and post-treatment icon 508 are displayed as icons for a series of the process steps.

Furthermore, display unit 10 displays first shutdown icon 510 for the first shutdown step performed when pretreatment unit 14 and analysis device 220 end the process steps without an error. Furthermore, display unit 10 displays second shutdown icon 518 for the second shutdown step performed when an error occurs while pretreatment unit 14 and analysis device 220 perform the process steps.

Further, as shown in FIGS. 10 to 13, when the user selects one of the icons for the series of the process steps, first shutdown icon 510, and second shutdown icon 518, display unit 10 displays an input screen for inputting the setting information for the process step corresponding to the selected icon. For example, the input screen is displayed with the selected icon displayed in a manner different than the other icons. For example, the setting screen of FIG. 10 displays that preparation icon 502 has been selected, and also displays input screen 502A for inputting the setting information for the process step corresponding to preparation icon 502, i.e., for the preparation.

Display unit 10 can thus visually display on setting screen 535 for which process step a setting, is, and thus allows the user to more easily input setting information. Furthermore, display unit 10 does not display the setting screen in a nested manner, and allows the user to recognize that the first shutdown and the second shutdown can be set.

Furthermore, second shutdown icon 518 is displayed in association with analyte analysis icon 506. In particular, in the present embodiment, analyte analysis icon 506 and second shutdown icon 518 are displayed such that the icons are connected by line image 513. Line image 513 allows the user to intuitively recognize that "the second shutdown is executed when an error occurs while pretreatment apparatus 1 and analysis device 220 perform the analyte analysis" and "the setting information for the second shutdown can be input at pretreatment apparatus 1."

Further, first shutdown icon 510 is displayed subsequent to post-treatment icon 508 in association with post-treatment icon 508. In particular, in the present embodiment, post-treatment icon 508 and first shutdown icon 510 are displayed such that the icons are connected by a line image. This line image allows the user to further intuitively recognize that the setting information for a step to shutdown the analyte analysis can be input at pretreatment apparatus 1. This allows the user to intuitively recognize that "the first shutdown is executed when pretreatment apparatus 1 and analysis device 220 have finished an analyte analysis without an error" and "the setting information for the first shutdown can be input at pretreatment apparatus 1."

(1-2) As has been discussed with reference to FIGS. 10 to 13, display unit 10 displays the process steps performed in pretreatment unit 14 and analysis device 220 in an order in which the process steps are performed. On the other hand, regardless of the order of performing the process steps in pretreatment unit 14 and analysis device 220, the user can display an input screen by selecting an icon corresponding to a process step.

For example, before displaying the input screen for the dummy analysis, the user can select post-treatment icon 508 to display the input screen for the post-treatment, and can input setting, information via that input screen.

This allows settings to be done for each process step regardless of the order of performing the process steps in pretreatment unit 14 and analysis device 220 and can thus provide the user with an increased degree of freedom in setting.

(1-3) Display unit 10 displays on setting screen 535 performance start button 514 for performing process steps in pretreatment unit 14 and analysis device 220. Further, performance start button 514 is adapted to be unselectable when no setting information set in pretreatment unit 14 (or pretreatment apparatus 1) and analysis device 220 is input.

In the present embodiment, as shown in FIG. 8, performance start button 514 can be caused to display x image 514a to allow the user to recognize that performance start button 514 is unselectable.

This can prevent pretreatment unit 14 and analysis device 220 from performing process steps while no setting information is set in pretreatment unit 14 and analysis device 220.

(1-4) Further, in the present embodiment, when an input screen for the setting information for a process step necessary for analysis device 220 to perform the analysis step is input and the setting information for that necessary process step is input via the input screen, x image 514a is deleted and the user can select performance start button 514. The process step necessary for analysis device 220 to perform the analysis step is a predetermined process step. In the present embodiment, the necessary process step includes preparation, an analyte analysis, and a post-treatment. When the setting information for at least one of these process steps is input, performance start button 514 becomes selectable. Once performance start button 514 has become selectable, x image 514a of performance start button 514 is erased.

This ensures that "process steps in pretreatment unit 14 and analysis device 220 can be performed after inputting the setting information for the process steps performed in pretreatment unit 14 and analysis device 220 is completed."

(1-5) Furthermore, as has been described with reference to FIGS. 8 and 9, of all of the process steps including a series of the process steps performed by pretreatment apparatus 1 and analysis device 220 (i.e., the preparation, the dummy analysis, the analyte analysis, the post-treatment, the first shutdown, the standby, and the second shutdown), only a process step that the user desires can be performed. For example, of the icons for all of the process steps, the user selects an icon corresponding to a desired process step and operates performance start button 514. The user can thus cause analysis system 20 to perform a step of the process steps that the user desires.

(1-6) For an input screen for a process step other than the pretreatment, setting, screen 535 is displayed when setting button 516 is operated while the FIG. 8 menu screen (or the pre-setting screen) is displayed. Furthermore, as shown in FIGS. 11 to 13, when setting screen 535 is displayed and the icon corresponding to the process step is selected, an input screen for the process step corresponding to the selected icon is displayed.

In contrast, for an input screen for the pretreatment, setting screen 535 is displayed when setting button 516 is operated while the FIG. 8 menu screen (or the pre-setting screen) is displayed, and the input screen for the pretreatment is displayed on setting screen 535. Thus, the input screen for the initial process, step (i.e., the pretreatment) of a series (or all) of the process steps performed by pretreatment apparatus 1 and analysis device 220 is displayed even when preparation icon 502 is not operated. When this is compared with a "pretreatment apparatus in which the input screen for the pretreatment is displayed when setting button 516 is operated with preparation icon 502 selected," the former can alleviate a burden on a user in displaying the input screen for the pretreatment.

Note that, as a modification, a process step corresponding to an input screen displayed on setting screen 535 displayed when setting button 516 is operated while the FIG. 8 menu screen (or the pre-setting screen) is displayed, may be another process step (e.g., the analyte analysis). The process step may thus be any process step insofar as it is a predetermined process step.

(1-7) Further, as shown in FIG. 8 and FIG. 9, in the pre-setting image, caution image 519 is displayed to caution the user in using analysis system 20. Further, the pre-setting image is an image that is necessarily displayed in order for analysis system 20 to perform the analysis step. Thus, pretreatment apparatus 1 can display caution image 519 in the pre-setting image that is necessarily displayed in order for analysis system 20 to perform the analysis step. This can help the user to recognize caution image 519.

(1-8) In addition, the series of the process steps are preparation, an analyte analysis, and a post-treatment. Further, display unit 10 displays icons for the preparation, the analyte analysis, and the post-treatment (that is, preparation icon 502, analyte analysis icon 506, and post-treatment icon 508) on setting screen 535 in a manner that can specify that the preparation is performed followed, by the analyte analysis followed by the post-treatment. This allows the user to intuitively recognize that analysis system 20 performs the preparation, the analyte analysis and the post-treatment in this order. Further, this allows the user to intuitively recognize that "the second shutdown is executed when an error occurs while pretreatment apparatus 1 and analysis device 220 perform the analyte analysis" and "the setting information for the second shutdown can be input at pretreatment apparatus 1."

(1-9) Further, pretreatment apparatus 1 and analysis device 220 can perform a dummy analysis to allow at least the series of the process steps to be performed without introducing in pretreatment apparatus 1 a sample to be analyzed, and display unit 10 displays dummy analysis icon 504 on setting screen 535 for the dummy analysis.

The dummy analysis that allows at least the series of the process steps to be performed without introducing in pretreatment apparatus 1 a sample to be analyzed can thus be performed, and an input screen for inputting the setting information for the dummy analysis can be displayed (see FIG. 11).

The series of the process steps performed when the dummy analysis is performed may be the series of the process steps or all of the process steps.

(1-10) Further, pretreatment apparatus 1 and analysis device 220 can perform a standby step for a period of time after one analysis step ends before the subsequent analysis step is performed, and display unit 10 displays standby icon 512 on setting screen 535 for the standby step.

Thus a standby step can be performed for a period of time after one analysis step ends before the subsequent analysis step is performed, and an input screen for inputting the setting information for the standby step can be displayed (see FIG. 13).

(2-1) In step S15 shown in FIG. 6, obtaining unit 846 obtains calibration curve information about a calibration curve used by analysis device 220 to analyze a sample, and an analysis result obtained by analysis device 220 using the calibration curve. The analysis result by analysis device 220 using the calibration curve is determined by analysis device 220 in step S10.

Subsequently, in step S16, control unit 84 associates the calibration curve information obtained by obtaining unit 846 with the analysis result obtained by obtaining unit 846, and stores them in the second table (see FIG. 5). Subsequently, as shown in FIG. 14, control unit 84 displays the analysis result and the calibration curve information associated with the analysis result on the same screen.

For example, there is a case in which when the user finished an analysis of a sample the user was unable to recognize that the analysis had an erroneous result and later (for example, several days later) it is found that the analysis has the erroneous result.

In that case, conventionally, the user has been required to cause a transition to a screen to display a list of calibration curves, and search for and retrieve a calibration curve associated with the analysis result that is found to be erroneous. This imposes a burden on the user.

Accordingly, display unit 10 of the present embodiment displays analysis result J and calibration curve information 410 on the same screen. Even when the user finished an analysis of a sample and thereafter (for example, several days later) it is found that the analysis has an erroneous result, the user can recognize information about a calibration curve, or calibration curve information 410, without a burden imposed on the user.

(2-2) Calibration curve information 410 includes calibration curve identification information 403 for identifying, a calibration curve. Even when an analysis result, is found to be erroneous, the user can easily recognize calibration curve identification information 403. Thus, for example, the user can easily recognize an applied calibration curve, based on the calibration curve identification information, on the screen that displays a list of calibration curves.

(2-3) Calibration curve information 410 includes reference sample identification information 404 which is information about a reference sample used to create a calibration curve. When the graph of the calibration curve is found to be erroneous for any reason, the user can recognize on which reference sample the erroneous calibration curve was based when it was created. As will be described hereinafter, the user can recognize that the graph of the calibration curve is erroneous when the user visually observes the screen shown in FIG. 15.

(2-4) Analysis system 20 may have a calibration curve created by a user's operation multiple times under the same analysis condition. In that case, the analysis system (or MS 200) analyzes a sample by using the latest created calibration curve. If an analysis result, is found to be erroneous, the user may want to determine whether the latest created calibration curve was used to analyze the sample. Accordingly, as shown in FIG. 14, calibration curve information 410 includes a calibration curve creation date and time 402. Thus, when an analysis result is found to be erroneous, the user can recognize the date and time when the calibration curve was created. Thus, when an analysis result is found to be erroneous, the user can determine whether the latest created calibration curve was used to analyze the sample.

(2-5) When calibration curve information 410 is designated (or selected), display unit 10 displays graph 602 representing a calibration curve identified by the calibration curve information, as shown in FIG. 15. When an analysis result is found to be erroneous, the user can specifically recognize which calibration curve was used to analyze a sample.

(2-6) As shown in FIG. 15, together with graph 602 indicating a calibration curve, display unit 10 also displays on the same screen in association with the graph analysis result 604 used when the calibration curve is created. For example, there is a case in which when the user finished an analysis of a sample the user was unable to recognize that the analysis had an erroneous result, and later (for example, several days later) it is found that the analysis has the erroneous result. In that case, the user can cause display unit 10 to display the graph of the calibration curve shown in FIG. 15. In graph 602 of the calibration curve, when there is analysis result 604 significantly deviating from graph 602, then, for example, the user can infer that there was an error in creating the calibration curve. That is, from graph 602 representing the calibration curve, and analysis result 604 used when the calibration curve was created, the user can recognize whether the graph representing the calibration curve is correct or incorrect.

(2-7) Display unit 10 displays a plurality of pieces of analysis result related information 302 (or analysis result J). Thus the user can recognize, for example, previous analysis result related information 302. Furthermore, when one of the plurality of pieces of analysis result related information 302 is designated (or selected), display unit 10 displays calibration curve information 410 about a calibration curve used to output the designated analysis result Thus, the user can recognize calibration curve information 410 for analysis result related information 302 of the plurality of pieces of analysis result related information 302 (or analysis result J) that is found to be erroneous.

(2-8) As shown in FIG. 4, pretreatment apparatus 1 stores a plurality of calibration curves K in the first table. Further, as shown in step S6 of FIG. 6, pretreatment apparatus 1 transmits to analysis device 220 a calibration curve used by analysis device 220. As shown in step S10 of FIG. 6, analysis device 220 analyzes a sample by using the calibration curve transmitted from the pretreatment apparatus. As the analysis device analyzes a sample by using a calibration curve designated by the pretreatment apparatus, the analysis device can be caused to analyze the sample, as controlled by the pretreatment apparatus.

Further, the plurality of calibration curves may be stored in analysis device 220, rather than pretreatment apparatus 1. However, it is preferable that pretreatment apparatus 1 hold the calibration curves, since pretreatment apparatus 1 causes display unit 10 to display the graph of a calibration curve, as shown in FIG. 15. If analysis device 220 should be configured to store a plurality of calibration curves (hereinafter also referred to as a configuration of a comparative example), pretreatment apparatus 1 and analysis device 220 both need to store the plurality of calibration curves. This invites less efficient storage than the analysis system of the present embodiment does.

Accordingly, as in the present embodiment, analysis device 220 does not store the plurality of calibration curves, and pretreatment apparatus 1 store the plurality of calibration curves. The analysis system of the present embodiment thus allows more efficient storage than the configuration of the comparative example.

[Modification]

Hereinafter, a modification of pretreatment apparatus 1 and analysis system 20 will be described.

(1) Display unit 10 may change an order of arranging icons corresponding to process steps depending on the type of analysis device 220 linked to pretreatment apparatus 1. For example, pretreatment apparatus 1 has a third table in which types of analysis devices are associated with orders in which process steps are performed. FIG. 16 shows an example of the third table. In the example of FIG. 16, an analysis device of a type A is associated with an order B in which process steps are performed.

For example, when an analysis device is newly connected to pretreatment apparatus 1, pretreatment apparatus 1 transmits a request signal to the connected analysis device for the type of the analysis device. The analysis device receives the request signal, and transmits an analysis device type signal to pretreatment apparatus 1. The analysis device type signal is a signal indicating the type of the analysis device.

When pretreatment apparatus 1 receives the analysis device type signal, pretreatment apparatus 1 refers to the third table of FIG. 16 to retrieve an order of performing process steps that is associated with the type of the analysis device identified from the analysis device type signal. Pretreatment apparatus 1 displays icons of a plurality of process steps in the retrieved order on the top screen and the setting screen.

Thus the analysis system allows appropriate settings in accordance with the type of the analysis device linked, and the user can confirm, in a list, process steps that need to be set.

In particular, as an analysis device connected to the pretreatment apparatus, MS 200 may not be connected and LC 100 may alone be connected, or LC 100 may not be connected and MS 200 may alone be connected. Thus, even when the analysis device is changed, etc., icons corresponding to process steps can be displayed based on the analysis system's proper order of performing the process steps.

(2) Further, display unit 10 may be adapted to be capable of changing, as desired, an order of arranging icons displayed on the setting screen. This change is, for example, made by an input made by a user via input unit 16. This enables the analysis system to change the order of arranging icons to be an order which facilitates the user to provide setting.

(3) Further, when setting information is input on an input screen for setting a first, process step, display unit 10 previously inputs and thus displays setting information on an input screen for setting a second process step relevant to the first process step.

For example, the first process step is a standby step (i.e., a process step corresponding to standby icon 512 in FIG. 8 or the like) and the second process step is the second shutdown step for the sake of illustration. The standby step and the second shutdown step are relevant in that analysis system 20 is stopped.

In such a case, when setting information predetermined for the first process step or the standby step (for example, turning off a pump in image 562 for the LC) is set, setting information predetermined for the second process step or the second shutdown step (for example, turning off a pump in image 552 for the LC) is also set. This can alleviate an operation done by a user to input setting information.

(4) Further, the present embodiment has been described such that when calibration curve information 410 shown in FIG. 14 is designated by a user, graph 602 of a calibration curve associated with calibration curve information 410 is displayed as shown in FIG. 15.

However, graph 602 may be included in calibration curve information 410 shown in FIG. 14. That is, display unit 10 may cause calibration curve information display area 400 to display graph 602 of the calibration curve. The user can thus directly recognize graph 602 of the calibration curve without designating calibration curve information 410. Further, pretreatment apparatus 1 may display graph 602, and an analysis result on graph 602, as shown in FIG. 15.

(5) Further, the present embodiment has been described such that calibration curve information 410 includes all of analysis information 401, calibration curve creation date and time 402, calibration curve identification information 403, and reference sample identification information 404.

However, calibration curve information 410 may include at least one of analysis information 401, calibration curve creation date and time 402, calibration curve identification information 403, and reference sample identification information 404. Further, which information is displayed as calibration curve information 410 may be selectable by the user.

(6) Further, the present embodiment has been described such that pretreatment apparatus 1 holds the table shown in FIG. 5. However, analysis device 220 may hold at least a portion of the table shown in FIG. 5. In such a configuration, pretreatment apparatus 1 will obtain from analysis device 220 information necessary for displaying the screen shown in FIG. 14 or the like.

Further, analysis system 20 may be composed of pretreatment apparatus 1, computing device 90, and analysis device 220. In that case, the tables of FIGS. 4 and 5 are held by computing device 90. Furthermore, the function of storage unit 12 and that of obtaining unit 846 are held by computing device 90. Furthermore, computing device 90 controls displaying provided by display unit 10 of pretreatment apparatus 1.

For example, in step S6 of FIG. 6, pretreatment apparatus 1 transmits an analysis condition to analysis device 220 and does not transmit any calibration curve. In step S8, analysis device 220 obtains the analysis condition. In step S10, analysis device 220 calculates analysis data (the first parameter, a value in area) based on the analysis condition. Analysis device 220 transmits the calculated analysis data to computing device 90. Computing device 90 derives an analysis result (or concentration) from the analysis data by using a calibration curve. Thereafter, computing device 90 incrementally updates the table of FIG. 5 based on the derived analysis result.

Then, when display unit 10 displays the image shown in FIG. 14, and the user selects analysis result related information 302, the selected position's coordinate information is transmitted to computing device 90. Computing device 90 displays in calibration curve information display area 400 calibration curve information based on the coordinate information. According to such a configuration, that is, as controlled by computing device 90, display unit 10 displays, on a single screen, an analysis result derived using a calibration curve from analysis data obtained by the analysis device based on an analysis condition, and calibration curve information about the calibration curve used to derive the analysis result.

(7) Furthermore, it has also been described that two analysis devices 220 (i.e., MS 100 and LC 200) are linked to pretreatment apparatus 1. However, any number of analysis devices 220 may be used that is one or more.

While an embodiment of the present invention has been described, it should be understood that the presently disclosed embodiment has been described for the purpose of illustration only and in a non-restrictive manner in any respect. The scope of the present invention is defined by the terms of the claims, rather than the above description, and is intended to include any modifications within the meaning and scope equivalent to the terms of the claims.

What is claimed is:

1. A pretreatment apparatus comprising:
at least one processor configured to implement;
a pretreatment unit configured to subject to a pretreatment a sample to be analyzed by an analysis device;
an analysis condition input unit configured to receive an analysis condition input;
a communication unit configured to transmit to the analysis device the analysis condition received by the analysis condition input unit;
a control unit configured to control the pretreatment unit, and control the analysis device based on the analysis condition transmitted to the analysis device;
a setting unit configured to set setting information for the pretreatment unit and the analysis device;
a setting information input unit configured to receive the setting information to be set in the setting unit; and
a display unit configured to display a setting screen for inputting the setting information at the setting information input unit,
the display unit being configured to
display icons each corresponding to a process step of a series of process steps of the pretreatment unit and the analysis device on the setting screen in a manner that can specify an order of performing the series of process steps,
display an icon for a first shutdown step and an icon for a second shutdown step in association with the icons each corresponding to a process step of the series of process steps, the first shutdown step being performed when the pretreatment unit and the analysis device end the process steps without causing an error, the second shutdown step being performed when the pretreatment unit and the analysis device end the process steps as an error is caused while the process steps are performed, and
when a user selects one of the icons each corresponding to a process step of the series of process steps, the icon for the first shutdown step, and the icon for the second shutdown step, display an input screen on the setting screen for inputting the setting information for a process step corresponding to the selected icon.

2. The pretreatment apparatus according to claim 1, wherein the display unit is configured to change an order of arranging the icons corresponding to the process steps, depending on a type of the analysis device.

3. The pretreatment apparatus according to claim 1, wherein, regardless of an order of performing the process steps in the pretreatment unit and the analysis device, the display unit is configured to display an input screen of the process step corresponding to the selected icon.

4. The pretreatment apparatus according to claim 1, wherein the display unit is configured to display on the setting screen a start button for starting performance in the pretreatment unit and the analysis device, and the start button is selectable after the setting information to be set in the pretreatment unit and the analysis device is input.

5. The pretreatment apparatus according to claim 1, wherein the display unit is configured to change as desired an order of arranging icons displayed on the setting screen.

6. The pretreatment apparatus according to claim 1, wherein when the setting information is input on the input screen for setting a first process step, the display unit is configured to input and display the setting information on the input screen for setting a second process step relevant to the first process step.

7. The pretreatment apparatus according to claim 1, wherein
the series of process steps includes preparation, an analyte analysis, and a post-treatment, and
the display unit is configured to display an icon for the preparation, an icon for the analyte analysis, and an icon for the post-treatment on the setting screen in a manner that can specify that the preparation is performed followed by the analyte analysis followed by the post-treatment.

8. The pretreatment apparatus according to claim 1, wherein
the pretreatment apparatus and the analysis device is configured to perform a dummy analysis in which the series of process steps is performed without introducing in the pretreatment apparatus the sample to be analyzed, and
the display unit is configured to display an icon on the setting screen for the dummy analysis.

9. The pretreatment apparatus according to claim 1, wherein
the pretreatment apparatus and the analysis device is configured to perform a standby step for a period of time after one analysis step ends before a subsequent analysis step starts, and
the display unit is configured to display an icon on the setting screen for the standby step.

10. An analysis system comprising the pretreatment apparatus according to claim 1 and an analysis device.

* * * * *